(12) United States Patent
Boukhny et al.

(10) Patent No.: US 8,414,123 B2
(45) Date of Patent: Apr. 9, 2013

(54) TORIC LENSES ALIGNMENT USING PRE-OPERATIVE IMAGES

(75) Inventors: Mikhail Boukhny, Laguna Niguel, CA (US); Steven Bott, Oviedo, FL (US)

(73) Assignee: Novartis AG, Basel (CH)

( * ) Notice: Subject to any disclaimer, the term of this patent is extended or adjusted under 35 U.S.C. 154(b) by 519 days.

(21) Appl. No.: 12/189,482

(22) Filed: Aug. 11, 2008

(65) Prior Publication Data

US 2009/0048608 A1 Feb. 19, 2009

Related U.S. Application Data

(60) Provisional application No. 60/955,528, filed on Aug. 13, 2007.

(51) Int. Cl.
*A61B 3/10* (2006.01)
*A61B 3/00* (2006.01)
*A61F 9/00* (2006.01)

(52) U.S. Cl.
USPC .......................... 351/212; 351/246; 606/107

(58) Field of Classification Search .................. 351/161, 351/212, 246; 606/107; 623/6.11, 6.12, 623/6.17, 6.34, 6.43, 6.46
See application file for complete search history.

(56) References Cited

U.S. PATENT DOCUMENTS

| | | | |
|---|---|---|---|
| 5,089,022 A | 2/1992 | Koester et al. | |
| 5,740,802 A | 4/1998 | Nafis et al. | |
| 5,740,803 A | 4/1998 | Gray et al. | |
| 5,867,210 A | 2/1999 | Rod | |
| 5,975,084 A | 11/1999 | Alpins | |
| 6,241,356 B1 | 6/2001 | Von Wallfeld et al. | |
| 6,352,519 B1 * | 3/2002 | Anis et al. ........................ | 604/22 |
| 7,146,983 B1 | 12/2006 | Hohla et al. | |
| 7,654,668 B2 | 2/2010 | Neuhann et al. | |
| 2002/0097378 A1 | 7/2002 | Saito et al. | |
| 2003/0053025 A1 | 3/2003 | Turner et al. | |
| 2003/0071893 A1 | 4/2003 | Miller et al. | |
| 2003/0120266 A1 | 6/2003 | Fujieda | |
| 2004/0100619 A1 | 5/2004 | Olivier et al. | |
| 2005/0025365 A1 | 2/2005 | Oosawa | |
| 2005/0117118 A1 | 6/2005 | Miller et al. | |
| 2005/0225721 A1 | 10/2005 | Harris et al. | |

(Continued)

FOREIGN PATENT DOCUMENTS

| | | |
|---|---|---|
| WO | WO 92/03989 | 3/1992 |
| WO | WO 01/28476 | 4/2001 |

(Continued)

OTHER PUBLICATIONS

European Search Report for Application No. 08162267.2, Publication No. EP2025305, Published Feb. 18, 2009, 3 pages.

(Continued)

*Primary Examiner* — Scott J Sugarman
*Assistant Examiner* — Mahidere Sahle
(74) *Attorney, Agent, or Firm* — Jonathan E. Prejean (57) ABSTRACT

Proper selection and centering of an intraocular lens (IOL) is provided. An image of an eye, which may be captured during pre-operative tests and provided to a program operable to calculate the power and axis orientation of the IOL, is used to determine the location and orientation of the IOL. This produces an output or placement guide used to properly center and orient an IOL within the eye.

22 Claims, 7 Drawing Sheets

U.S. PATENT DOCUMENTS

2006/0247659 A1  11/2006  Moeller et al.
2007/0055222 A1* 3/2007  Hohla et al. .................. 606/12
2008/0247616 A1  10/2008  Pescatore et al.

FOREIGN PATENT DOCUMENTS

| WO | WO 01/78584    | 10/2001 |
|----|----------------|---------|
| WO | WO 01/89373    | 11/2001 |
| WO | WO 02/064031   | 8/2002  |
| WO | WO 02/074248   | 9/2002  |
| WO | WO 03/022137   | 3/2003  |
| WO | WO 2006/044056 | 4/2006  |
| WO | WO 2008/008044 | 1/2008  |

OTHER PUBLICATIONS

Arbelaez, et. al., "Clinical Outcomes of Corneal Vertex Versus Central Pupil References With Aberration-Free Ablation Strategies and LASIK," Dec. 2008, Investigative Ophthalmology & Visual Science, Dec. 2008, Lnkd-Pubmed: 18658090, vol. 49, NR. 12, pp. 5287-5294, XP002584895, ISSN: 1552-5783, Materials and Methods: p. 5287 Figure 5.

Ma, et. al., "Simple Method for Accurate Alignment in Toric Phakic and Aphakic Intraocular Lens Implantation," Journal Cataract and Refractive Surgery, Surgery, Fairfax, VA Lnkd-DOI: 10.10163/J. JCRS.2008.04.041, vol. 34, No. 10, Oct. 1, 2008, pp. 1631-1636, XP025627296, ISSN: 0886-3350.

Nguyen, et. al., "Digital Overlay Technique for Documenting Toric Intraocular Lens Axis Orientation," Oct. 2000, Journal of Cataract and Refractive Surgery, Oct. 2000, Lnkd-PubMed: 11033397, vol. 26, NR. 10, pp. 1496-1504, XP002584785, ISSN: 0886-3350.

Yang, et. al., "Pupil Location Under Mesopic, Photopic, and Pharmacologically Dilated Conditions," Investigative Ophthalmology & Visual Science, Association for Research in Vision and Ophthalmology, US, vol. 43, No. 7, Jul. 1, 2002, pp. 2508-2512, XP002537709, ISSN: 0146-0404, Pupil Center Location; p. 2509-2510, Discussion, p. 2511-2512.

International Search Report for International Application No. PCT/US2010/024482, 4 pages.

Written Opinion for International Application No. PCT/US2010/024482, 6 pages.

International Search Report for International Application No. PCT/US2010/024483, 4 pages.

Written Opinion for International Application No. PCT/US2010/024483, 5 pages.

European Search Report for Application No. 11162125.6, Publication No. EP2353546, Published Aug. 10, 2011, dated Jun. 20, 2011, 3 pages.

* cited by examiner

PRIOR ART

TORIC LENSES ALIGNMENT USING PRE-OPERATIVE IMAGES

CROSS-REFERENCE TO RELATED APPLICATIONS

This application claims priority under 35 U.S.C. §119 to U.S. Provisional Patent Application No. 60/955,528, filed Aug. 13, 2007, the entire contents of which are incorporated herein by reference.

TECHNICAL FIELD OF THE INVENTION

The present invention relates generally to the field of intraocular lenses (IOL), and, more particularly, to methods and systems for determining placement and orientation of an implanted IOL.

BACKGROUND OF THE INVENTION

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

The placement of an IOL is very important in order to ensure the best possible vision for patient's with cataracts. Oftentimes there is not a good feedback process during surgery to ensure that the IOL is properly placed and oriented within the eye.

SUMMARY OF THE INVENTION

Embodiments of the present invention provide a system and method operable to provide for the proper selection and centering of an intraocular lens (IOL) that substantially addresses the above identified needs. An image of an eye, which may be captured during pre-operative tests and provided to a program operable to calculate the power and axis orientation of the IOL, is used to determine a location and orientation of the IOL. A placement guide is produced for use in properly centering and orienting an IOL within the eye.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DESCRIPTION OF THE INVENTION

Preferred embodiments of the present invention are illustrated in the FIGs., like numerals being used to refer to like and corresponding parts of the various drawings.

Embodiments of the present invention substantially address the above identified needs as well as others. Intraocular Lenses (IOL) have opened new possibilities for treating cataractous lenses which are removed by a surgical technique. The diseased lens, once removed, is replaced by an artificial lens. Proper vision following the procedure depends greatly on the placement and orientation of the IOL.

Figure 1:
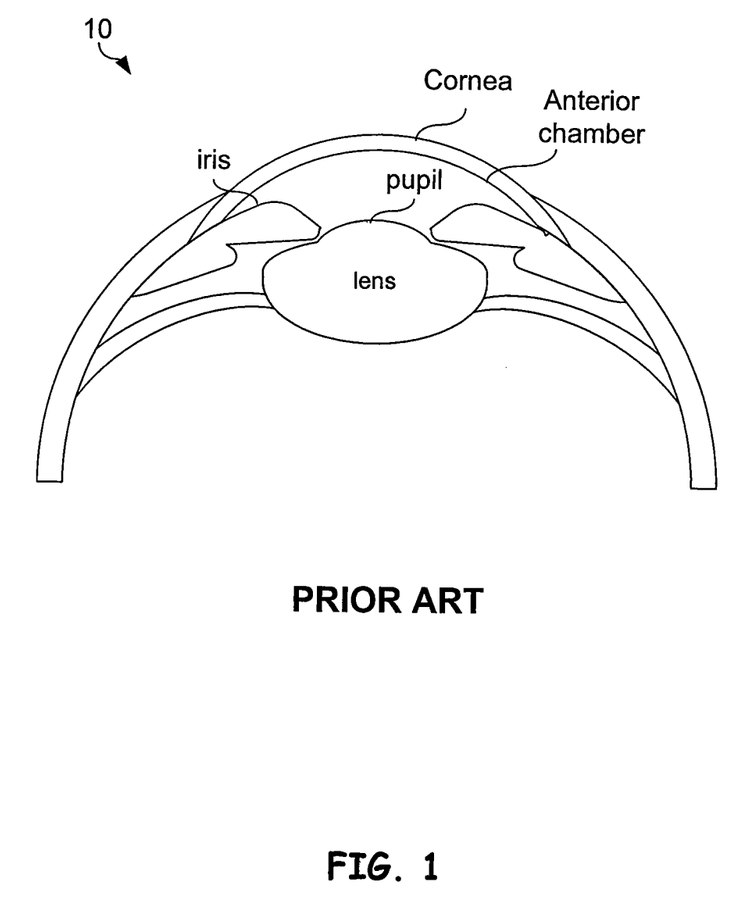
FIG. 1 depicts selected tissues of the eye.

FIG. 1 depicts selected tissues of eye 10. These include the iris, pupil, cornea and lens which, when cataractous, may be removed and replaced with an IOL. The placement of an IOL is a key component to the best possible vision for the patient.

Figure 2:
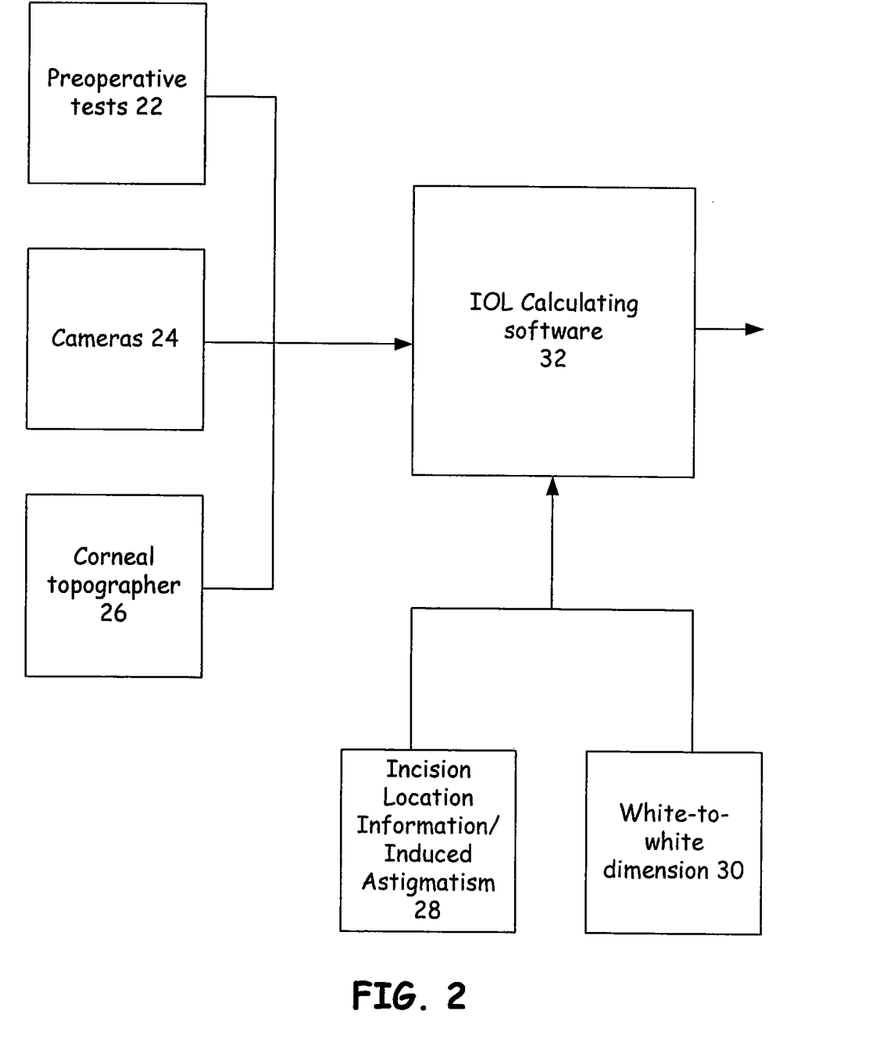
FIG. 2 depicts various inputs which may be used by an IOL calculating computer program to calculate the power of a "toric lens," and the location and axis orientation of that IOL lens used to replace lens tissue within eye in accordance with embodiments of the present invention.

FIG. 2 depicts various inputs which may be used by a computer program, IOL calculating program 32, to calculate the power of a toric lens, and the location and axis orientation of that IOL lens used to replace lens tissue within eye 10. These inputs include pre-operative tests 22 used to determine the center of the eye, video or digital cameras 24 used to produce eye images with sclera vessels, and cornea topographer 26. Incision location information and surgically induced astigmatism information 28, and white-to-white dimension 30 are also provided. The measured data along with these representations of the eye along with incision location information may be used by program 32. In one embodiment, IOL calculation program 32 may be Alcon's "toric calculator" that is executed on a desktop computer or cataract removal console such as Alcon's "Infiniti Vision System." The image of the eye captured during pre-operative tests may be uploaded into (provided to) software program 32.

These inputs are used by IOL calculating program 32 to produce an image or like representation of the eye with the location and orientation axis of the IOL identified. Knowing the center of the eye is keenly important for the proper centering and alignment of an IOL.

Figure 3:
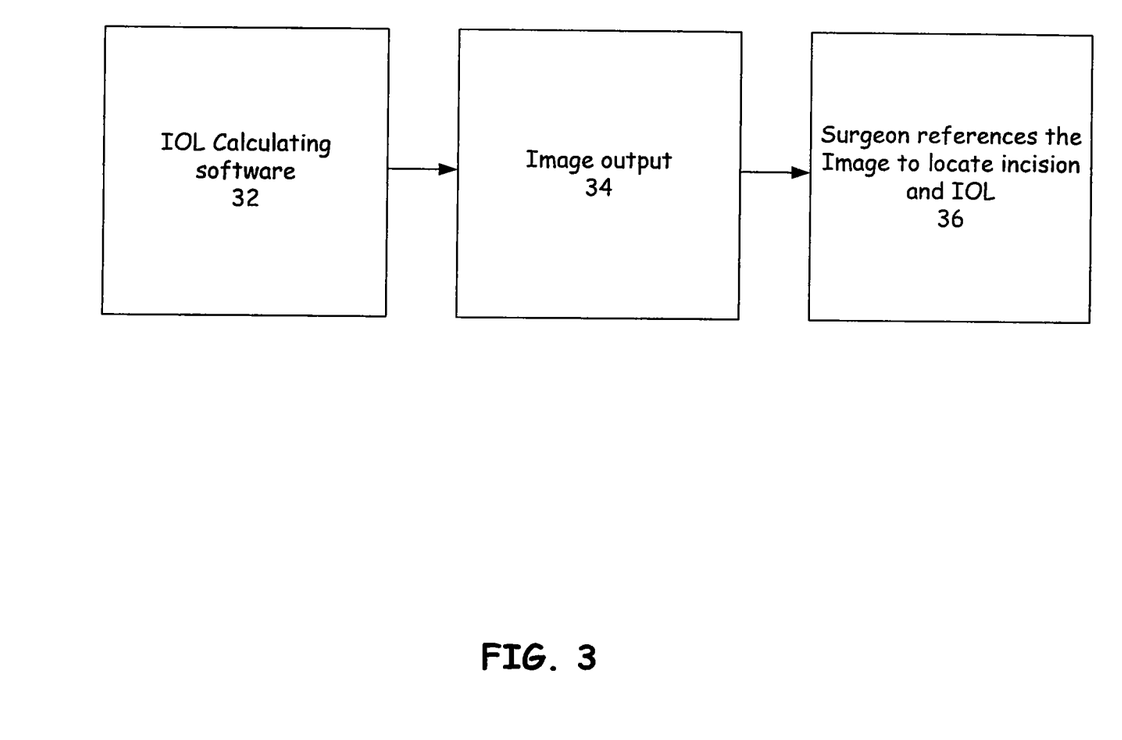
FIGS. 3, 4 and 5 present different ways in which information may be used to generate placement guides in accordance with embodiments of the present invention.
Figure 4:
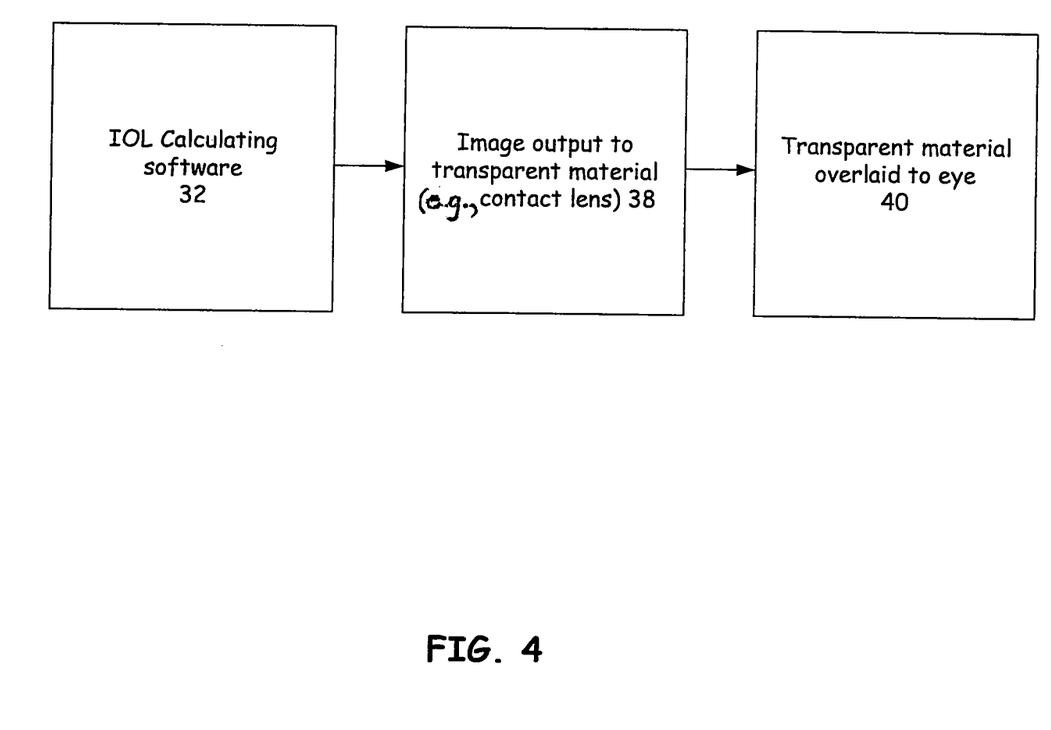
Figure 5:
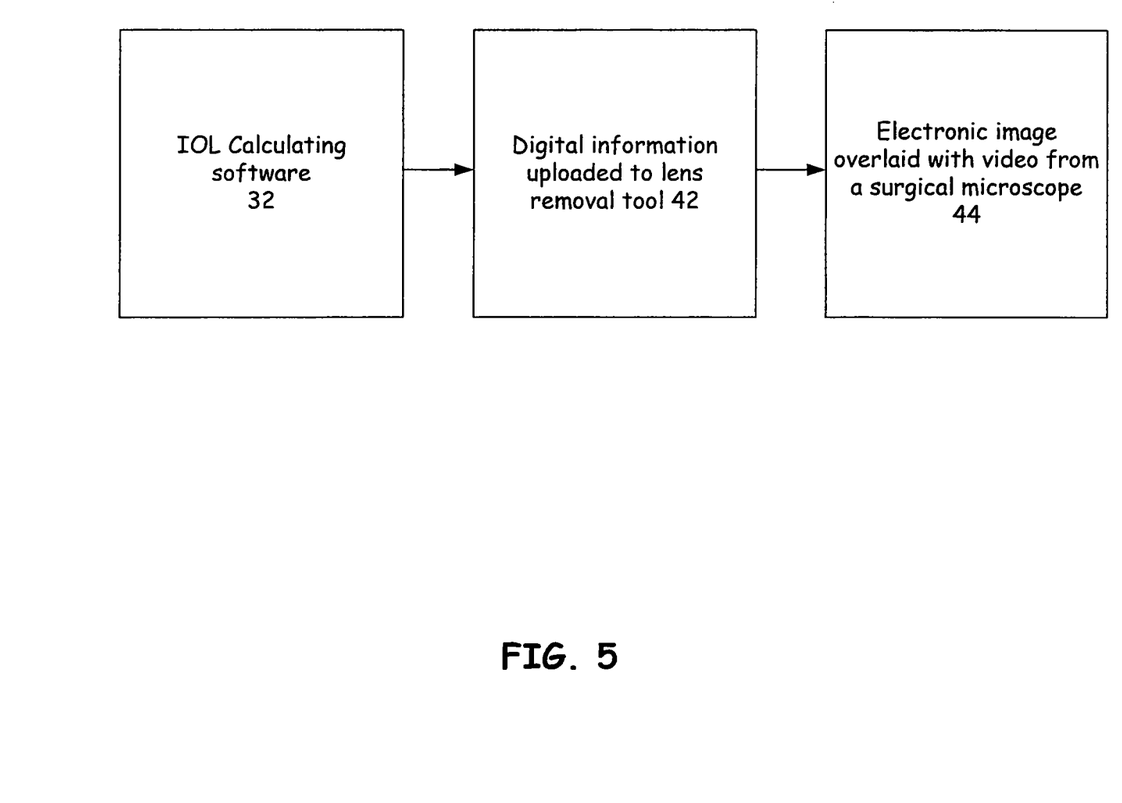

FIGS. 3, 4 and 5 discuss different ways in which this information may be used. In FIG. 3 software program 32 may provide an output such as a simple printed picture in process 34 that becomes available to a surgeon during surgery. This allows a surgeon to reference the image and characteristic vessels therein to locate the incision and orient the IOL in process 36.

FIG. 4 describes another possibility for how location and orientation information may be applied. Again software program 32 produces or outputs orientation and location information. In this instance orientation and location information may be printed on a transparent material which may include a contact lens in process 38. This image on the transparent material may be overlaid by the surgeon directly on the patient's eye to match the characteristics of the patient's eye within process 40. The IOL may then be centered and rotated to match markers on the transparent material.

A third process is depicted in FIG. 5. Here software program 32 provides an electronic output which may be uploaded on a lens removal console 42. The console may receive video from an optical microscope which recognizes vessels and overlays live optical video images in process 44 to previously uploaded pre-operative images. The video information may then be used to advise the surgeon in how to rotate and place the IOL.

Figure 6:
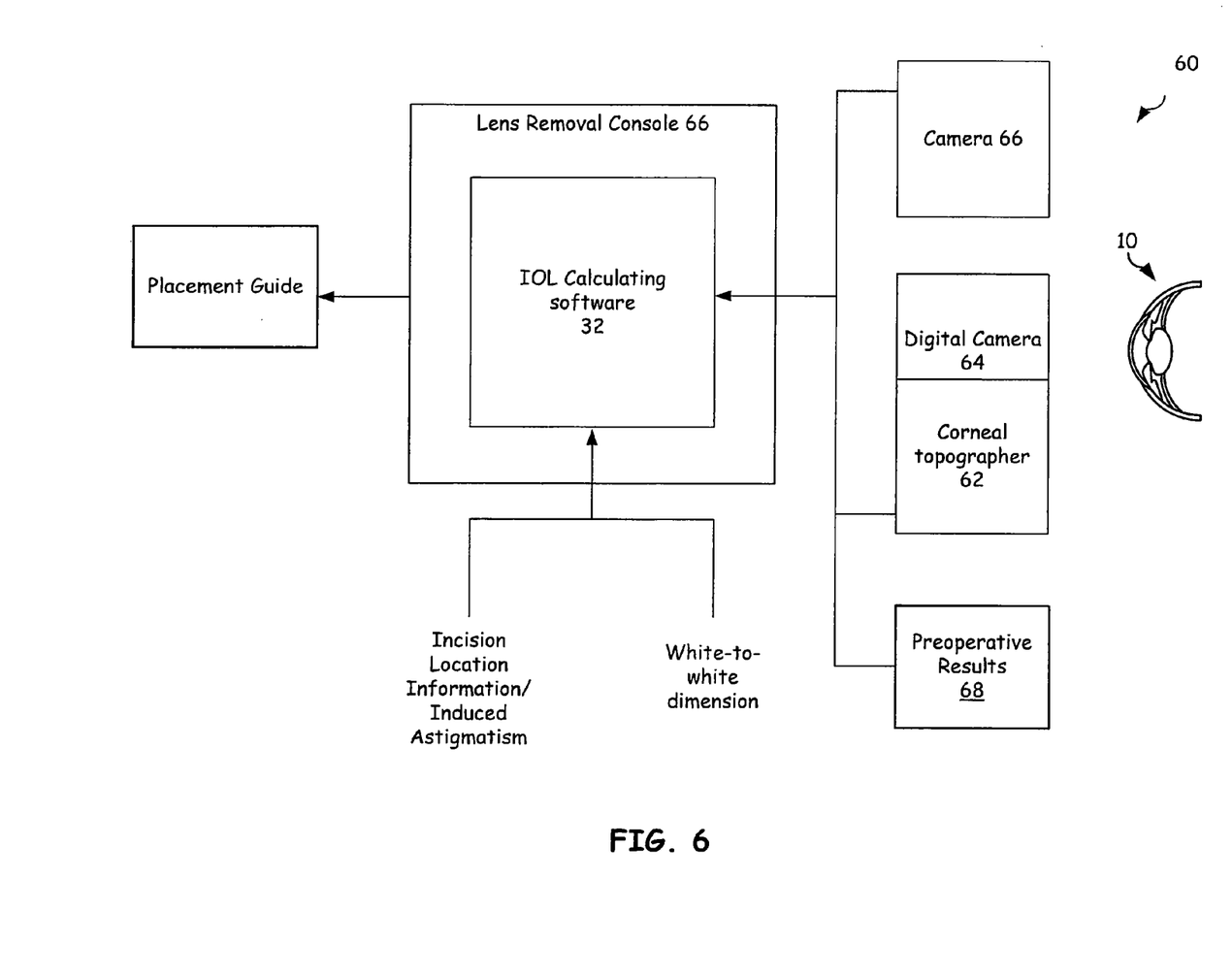
FIG. 6 depicts a system operable to facilitate placement of an IOL in accordance with embodiments of the present invention.

FIG. 6 depicts a system operable to facilitate placement of an IOL. System 60 includes Corneal topographer 62 equipped with a digital camera 64 to produce a surface profile and image of eye 10 that includes vessels in the sclera. Alternatively a separate camera 66 can be used to take the picture of patient's eye 10. Data from the topographer 62 along with incision location and induced astigmatism are input into program 32 to calculate power of the toric lens and the axis orientation. The program can reside on the web, on an office PC, or on the cataract removal console such as the Infiniti Vision System (Alcon). The image of the eye captured during preoperative test 68 at the same time when topography was performed, or at least in the same patient orientation, is uploaded into the same program. The output is the image of the eye with the axis overlaid. It is also possible to label the "center" of the eye on the same image, however determined during the preoperative tests. The center of the eye is important for proper centering of IOL.

The image of the eye 10 with the vessels, overlaid steep axis of the toric lens and the center of the eye 10, as well as approximate "up" arrow can then be used in three ways to generate reference diagrams as described in FIGS. 3-5.

Embodiments of the present invention may take advantage of computer Image analysis of digital images of the eye taken during a pre-surgery session and again during the surgical procedure to register the eye, and a microscope adapted with a heads-up display (HUD) to provide the surgeon with visual feedback to help orient visually the IOL during the implantation procedure.

Digital image analysis allows measurements taken during the pre-surgery session by a corneal topographer to facilitate selecting the IOL's optical characteristics. The selection of IOL cylinder power is made on the basis of corneal topography measurements as well as other anatomic measurements of the eye, such as eye length and anterior chamber depth. As part of the topography measurement, a video snapshot of the eye can be captured with a camera incorporated into the topographer and situated at a known position and orientation with respect to the eye and topographic measurement apparatus such that precise "mapping" of the snapshot of the eye to the corneal topography measurement can be made.

The camera, camera optics, camera electronics and eye illumination system can be chosen to allow video snapshots of the eye to be taken simultaneously with the topographic measurement (to prevent eye motion artifacts) and to permit an mage of sufficient contrast, resolution and field of view to allow clear visibility of scleral blood vessels and other eye features such as the limbus.

First, the image can be simply printed out and posted in front of the surgeon during the surgery. The surgeon can then reference characteristic vessels to position an incision appropriately and to orient the IOL relative to the scleral blood vessels. This may obviate the need for manual eye marking with a "sharpie" as typically done in the prior art, but will likely provide rather limited accuracy. Pre-operative biometry information along with the eye's image is input into the program which calculates optimum toric lens and its orientation in the eye.

Second, the image of the eye including the steep axis and location of the incision can be printed out on a transparent plastic, for example transparencies or a contact lens. In order to scale the image properly, the "white-to-white" dimension input into the program is used. The toric lens is implanted into the eye and oriented approximately. There is a pattern printed on the lens which indicates direction of the axis. For example, 3 dots in the peripheral part of the optic may be used to indicate the axis. After the lens is placed and approximately oriented, the transparent plastic is overlaid on the eye and oriented to match vessels. Then the lens is centered and oriented so that the axis marked on the lens is superimposed with the axis printed on the plastic with the lens superimposed with the "center" printed on the plastic.

Another method is to upload the image of the eye with the vessels, axis and center onto the lens removal console. An image from the surgical microscope is transferred to the console as well and compared with the uploaded image. Sclera vessels serve as landmarks to overlay the two images. Lens orientation is determined by locating the distinguishing features on the lens. The surgeon is presented with the captured image of the eye on the screen of the console and advised visually and/or through voice confirmation where to move and/or rotate the lens. There are other advantages in having the eye image and biometry information input into the console. At the beginning of the procedure there can be a step on the console for providing supplementary information to the surgeon relating to where to make an incision and information on incision width. If the location or width of the incision are altered, the new information can be input back into the console to analyze potential differences in recommended lens selection and/or lens orientation. This can be easily accomplished if the IOL calculation program 32 is loaded on the console. The console can also be equipped with a barcode reader, or other equipment tracking system, and the IOL and tools (e.g., knife) used in surgery can be scanned so that the console can double check the incision width as well as the lens selection.

Figure 7:
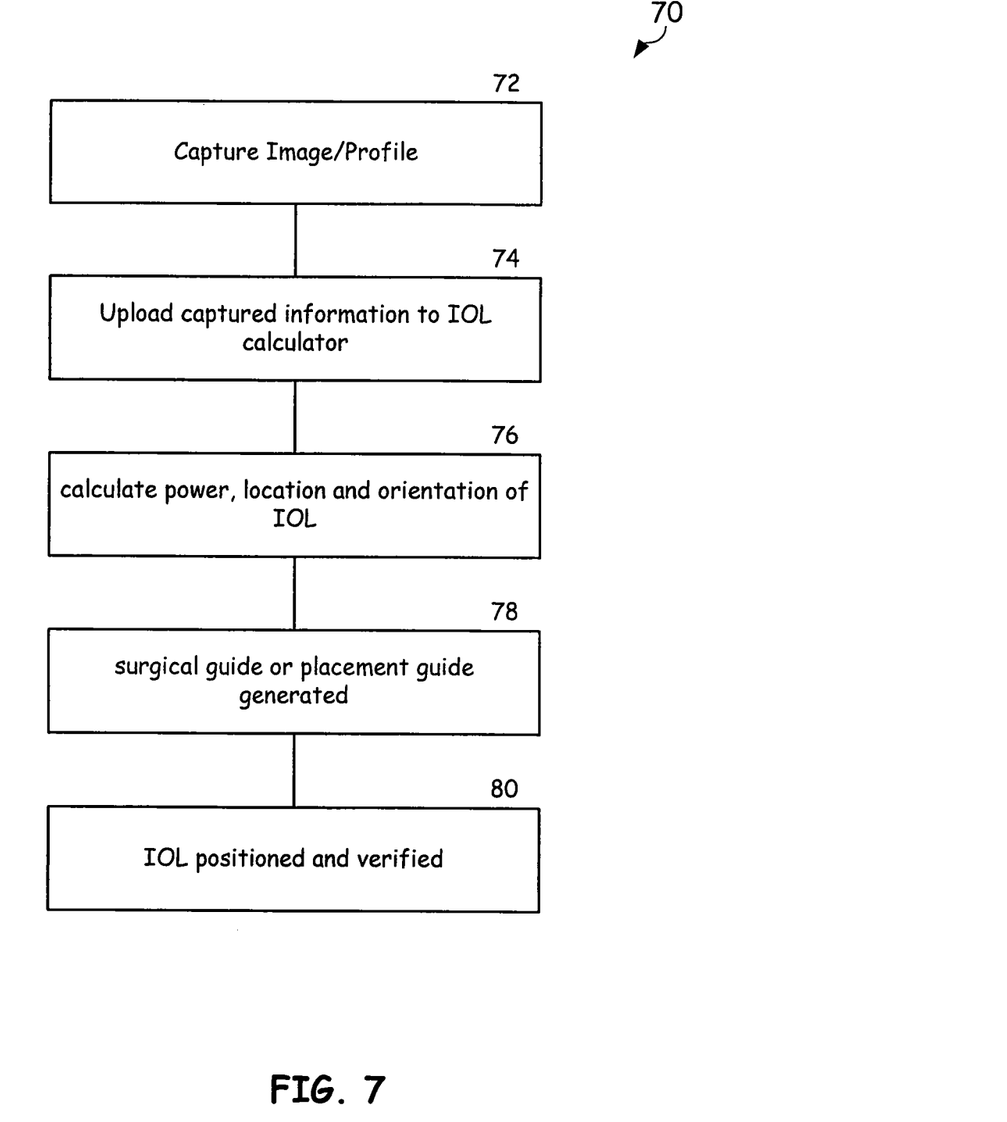
FIG. 7 provides a logic flow diagram in accordance with embodiments to the present invention of a process operable to place an IOL within an eye.

FIG. 7 provides a logic flow diagram in accordance with embodiments to the present invention of a process operable to place an IOL within an eye. Operations 70 begin with Step 72 where an image or other information about an eye in which the IOL is to be implanted is captured. Additionally planned incision location information and induced astigmatism information as well as white-to-white measurements may be captured as well. In Step 74 the captured information may be uploaded (provided) to an IOL calculator. This IOL calculator in Step 76 may calculate the power of the IOL as well as the location and orientation of the IOL within the eye. In Step 78 a surgical guide or placement guide may be generated to facilitate placement of the IOL within the eye. This placement guide may be a simple photograph available to the surgeon so that the surgeon may reference a picture and characteristics therein to locate the incision and orient the lens. Alternatively this placement guide may take the form of a transparent material, such as a contact placed over the eye, wherein placement guide information is printed on the transparent material. The transparent placement guide can thus be overlaid directly on the patient's eye by the surgeon in order to match the actual vessels there. The lens may then be centered and rotated to match markers on the transparent material. Alternatively, the placement guide may be electronic and overlaid with real time video information. The video information may be captured by a surgical microscope and transmitted to a lens removal console wherein processing modules within the lens removal console recognize and match structures from the placement guide to the live images. The lens removal console can recognize the lens marks and advise the surgeon on how to rotate and place the lens. In Step 80 the IOL is placed with the aid of the surgical or placement guide wherein the placement of the IOL may also be verified.

In summary, embodiments of the present invention provide for the proper selection and centering of an intraocular lens (IOL). An image of an eye, which may be captured during pre-operative tests and provided to a program operable to calculate the power and axis orientation of the IOL, is used to determine the location and orientation of the IOL. This produces an output or placement guide that can be used to properly center and orient an IOL within the eye.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention is described in detail, it should be understood that various changes, substitutions and alterations can be made hereto without departing from the spirit and scope of the invention as described.

What is claimed is:

1. A method to place an intraocular lens (IOL), the method comprising:
    capturing pre-operative information associated with an eye in an undilated state in which an IOL is to be implanted, the pre-operative information comprising a pre-operative image of the eye;
    capturing incision location information and induced astigmatism information associated with the eye in which an IOL is to be implanted;
    providing the information to an IOL calculating software program operable to calculate a location and orientation of the IOL within the eye; and
    generating a placement guide operable to assist a surgeon in placing the IOL within the eye, the placement guide comprising a registered image of the eye registered to the pre-operative image of the eye and further comprising the location and orientation of the IOL generated based on the pre-operative information.

2. The method of claim 1, further comprising using the placement guide to verify placement of the IOL within the eye.

3. The method of claim 1, wherein the information associated with the eye comprises a surface profile and/or image of the eye, wherein the image includes vessels within the sclera.

4. The method of claim 3, wherein a corneal topographer coupled to a digital camera captures the surface profile and/or image.

5. The method of claim 1, wherein the placement guide comprises an image that a surgeon may reference to position the incision and the IOL.

6. The method of claim 1, wherein the placement guide comprises an image on transparent material that a surgeon may reference to position the incision and the IOL.

7. The method of claim 6, wherein the image is located on a contact lens operable to be placed on the eye.

8. The method of claim 1, wherein the placement guide comprises an placement guide image combined with an image from a surgical microscope, within a lens removal console.

9. The method of claim 8, wherein the lens removal console is operable to advise the surgeon placing the IOL.

10. A method to place an intraocular lens (IOL), the method comprising:
    capturing pre-operative information associated with an eye in an undilated state in which an IOL is to be implanted, the pre-operative information comprising a pre-operative image of the eye;
    capturing planned incision location information associated with the eye in which an IOL is to be implanted;
    capturing-induced astigmatism information associated with the eye in which an IOL is to be implanted;
    providing the information to an IOL calculating software program operable to calculate a location and orientation of the IOL within the eye;
    calculating the location and orientation of the IOL within the eye; and
    generating a placement guide operable to assist a surgeon in placing the IOL within the eye, the placement guide comprising a registered image of the eye registered to the pre-operative image of the eye and further comprising the location and orientation of the IOL generated based on the pre-operative information.

11. The method of claim 10, further comprising:
    providing the surgeon feedback associated with the location and orientation of the IOL within the eye; and
    using the placement guide to verify placement of the IOL within the eye.

12. The method of claim 10, wherein the information associated with the eye comprises a surface profile and/or image of the eye, wherein the image includes vessels within the sclera.

13. The method of claim 12, wherein a corneal topographer coupled to a digital camera captures the surface profile and/or image.

14. The method of claim 10, wherein the placement guide comprises an image that a surgeon may reference to position the incision and the IOL.

15. The method of claim 10, wherein the placement guide comprises an image on transparent material that a surgeon may reference to position the incision and the IOL.

16. The method of claim 15, wherein the image is located on a contact lens operable to be placed on the eye.

17. The method of claim 10, wherein the placement guide comprises an placement guide image combined with an image from a surgical microscope, within a lens removal console.

18. The method of claim 17, wherein the lens removal console is operable to advise the surgeon placing the IOL.

19. A Lens removal console operable to facilitate placement of an intraocular lens (IOL), comprising:
   at least one input port operable to receive:
      pre-operative information associated with an eye in an undilated state in which an IOL is to be implanted, the pre-operative information comprising a pre-operative image of the eye;
      planned incision location information associated with the eye in which an IOL is to be implanted; and
      induced astigmatism information associated with the eye in which an IOL is to be implanted;
   a processing module and associated memory coupled to the at least one input port, the processing module operable to execute an IOL calculating software program operable to:
      calculate a location and orientation of the IOL within the eye from:
         the pre-operative information associated with an eye in which an IOL is to be implanted;
         the planned incision location information associated with the eye in which an IOL is to be implanted; and
         the induced astigmatism information; and
      generate a placement guide operable to assist a surgeon in placing the IOL within the eye, the placement guide comprising a registered image of the eye registered to the pre-operative image of the eye and further comprising the location and orientation of the IOL generated based on the pre-operative information.

20. The Lens removal console of claim 19, wherein a Corneal topographer coupled to a digital cameral captures the information associated with the eye and wherein the information comprises vessels within the sclera.

21. The Lens removal console of claim 19, wherein the placement guide comprises:
   an image that a surgeon may reference to position the incision and the IOL;
   an image located on a contact lens that a surgeon may reference to position the incision and the IOL; and/or
   a placement guide image combined with an image from a surgical microscope, within the lens removal console.

22. The Lens removal console of claim 19, wherein the lens removal console is operable to advise the surgeon placing the IOL.

* * * * *